US008088872B2

United States Patent
Chen et al.

(10) Patent No.: US 8,088,872 B2
(45) Date of Patent: Jan. 3, 2012

(54) PROCATALYST COMPOSITION INCLUDING SILYL ESTER INTERNAL DONOR AND METHOD

(75) Inventors: Linfeng Chen, Sugar Land, TX (US); Tak W. Leung, Houston, TX (US); Tao Tao, Houston, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 12/622,889

(22) Filed: Nov. 20, 2009

(65) Prior Publication Data

US 2010/0130709 A1 May 27, 2010

Related U.S. Application Data

(60) Provisional application No. 61/117,820, filed on Nov. 25, 2008.

(51) Int. Cl.
*C08F 4/50* (2006.01)
(52) U.S. Cl. ................................ 526/125.3
(58) Field of Classification Search ............... 526/125.3
See application file for complete search history.

(56) References Cited

U.S. PATENT DOCUMENTS

| | | | |
|---|---|---|---|
| 4,336,360 A | 6/1982 | Giannini et al. |
| 4,442,276 A | 4/1984 | Kashiwa et al. |
| 4,460,701 A | 7/1984 | Terano et al. |
| 4,540,679 A | 9/1985 | Arzoumanidis et al. |
| 4,547,476 A | 10/1985 | Terano et al. |
| 4,816,433 A | 3/1989 | Terano et al. |
| 4,829,037 A | 5/1989 | Terano et al. |
| 4,927,797 A | 5/1990 | Ewen |
| 4,971,937 A | 11/1990 | Albizzati et al. |
| 4,990,479 A | 2/1991 | Ishimaru et al. |
| 5,028,671 A | 7/1991 | Kioka et al. |
| 5,034,361 A | 7/1991 | Job et al. |
| 5,066,737 A | 11/1991 | Job |
| 5,066,738 A | 11/1991 | Ewen |
| 5,077,357 A | 12/1991 | Job |
| 5,082,907 A | 1/1992 | Job |
| 5,106,806 A | 4/1992 | Job |
| 5,106,807 A | 4/1992 | Morini et al. |
| 5,146,028 A | 9/1992 | Job |
| 5,151,399 A | 9/1992 | Job |
| 5,153,158 A | 10/1992 | Kioka et al. |
| 5,229,342 A | 7/1993 | Job |
| 5,247,031 A | 9/1993 | Kioka et al. |
| 5,247,032 A | 9/1993 | Kioka et al. |
| 5,432,244 A | 7/1995 | Rebhan |
| 5,539,309 A | 7/1996 | Van Wyk et al. |
| 6,391,985 B1 | 5/2002 | Goode et al. |
| 6,451,939 B1 * | 9/2002 | Britovsek et al. ........... 526/161 |
| 6,657,025 B2 | 12/2003 | Blackmon et al. |
| 6,825,146 B2 | 11/2004 | Kilty et al. |
| 6,960,635 B2 | 11/2005 | Stevens et al. |
| 7,388,061 B2 | 6/2008 | Gao et al. |
| 2005/0096389 A1 | 5/2005 | Gao et al. |
| 2005/0239636 A1 | 10/2005 | Gao et al. |

FOREIGN PATENT DOCUMENTS

| | | |
|---|---|---|
| CN | 1169845 C | 10/2004 |
| CN | 1580034 A | 2/2005 |
| EP | 0045977 B1 | 1/1987 |
| EP | 0671417 A2 | 9/1995 |
| EP | 1042372 A1 | 10/2000 |
| GB | 630951 | 10/1949 |
| WO | 00/63261 A1 | 10/2000 |
| WO | 03/068828 A1 | 8/2003 |

OTHER PUBLICATIONS

Djerourou, Abdel-Hafid, et al., Tetrahedron Letters, vol. 32, No. 44, pp. 6325-6326, 1991.

* cited by examiner

*Primary Examiner* — Ling Choi
*Assistant Examiner* — Sonya Wright
(74) *Attorney, Agent, or Firm* — Whyte Hirschboeck Dudek SC

(57) ABSTRACT

The present disclosure provides silyl esters and silyl diol esters suitable as internal electron donors in procatalysts for polymer production. Disclosed are procatalyst compositions formed from a procatalyst precursor and an internal electron donor that is a silyl ester or a silyl diol ester. The procatalyst compositions can be used with a cocatalyst and optionally an external electron donor and/or an activity limiting agent to form a Ziegler-Nana catalyst composition. The present catalyst compositions exhibit high catalyst activity and form olefin-based polymers with broad molecular weight distribution, favorable flexural modulus, and high isotacticity.

16 Claims, No Drawings

PROCATALYST COMPOSITION INCLUDING SILYL ESTER INTERNAL DONOR AND METHOD

CROSS REFERENCE TO RELATED APPLICATION

The present application claims priority to U.S. patent application Ser. 61/117,820, filed on Nov. 25, 2008, the entire content of which is incorporated by reference herein.

BACKGROUND

The present disclosure relates to silyl esters and the incorporation of the same in catalyst compositions and the process of making olefin-based polymers using said catalyst compositions.

Worldwide demand for olefin-based polymers continues to grow as applications for these polymers become more diverse and more sophisticated. Known are Ziegler-Natta catalyst compositions for the production of olefin-based polymers. Ziegler-Natta catalyst compositions typically include a procatalyst containing a transition metal halide (i.e., titanium, chromium, vanadium), a cocatalyst such as an organoaluminum compound, and optionally an external electron donor. Ziegler-Natta catalyzed olefin-based polymers typically exhibit a narrow range of molecular weight distribution. Given the perennial emergence of new applications for olefin-based polymers, the art recognizes the need for olefin-based polymers with improved and varied properties. Desirable would be Ziegler-Natta catalyst compositions for the production olefin-based polymers with broad molecular weight distribution.

SUMMARY

The present disclosure is directed to silyl ester compounds and the application of the same in catalyst compositions. The silyl ester-containing catalyst compositions of the present disclosure exhibit high activity and produce olefin-based polymers with broad molecular weight distribution and improved flexural modulus while maintaining high isotacticity.

In an embodiment, a silyl ester is provided. The silyl ester has the structure (I):

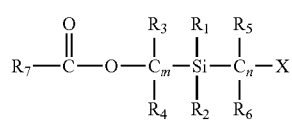

wherein m and n are each an integer from 1 to 5. The symbols m and n each denote a hydrocarbyl with the same number of carbon atoms. $R_1$-$R_7$ are the same or different and each is selected from hydrogen, a substituted hydrocarbyl group having 1 to 20 carbon atoms, an unsubstituted hydrocarbyl group having 1 to 20 carbon atoms, and combinations thereof. X is an electron donating group containing O, S, N, and/or P atom(s).

In an embodiment, $R_7$ is a benzene-ring-containing group. The benzene-ring-containing group optionally may be substituted with one or more of the following: a $C_{1-20}$ alkyl group, a $C_{1-20}$ alkoxy group, a $C_{1-20}$ alkoxycarbonyl group, a halogen atom, and any combinations thereof.

In an embodiment, a silyl diol ester is provided. The silyl diol ester has the following structure (II):

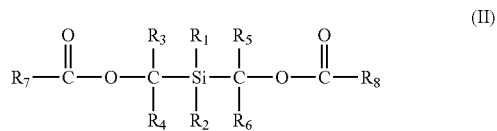

wherein $R_1$-$R_8$ are the same or different and each is selected from hydrogen, a substituted hydrocarbyl group having 1 to 20 carbon atoms, an unsubstituted hydrocarbyl group having 1 to 20 carbon atoms, and combinations thereof.

In an embodiment, one or both of $R_7$ and $R_8$ is a benzene-containing group.

In an embodiment, the silyl diol ester has the structure (III) as follows:

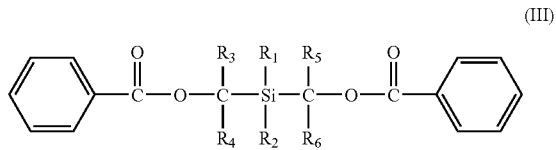

wherein $R_3$-$R_6$ are hydrogen, $R_1$ and $R_2$ are the same or different and each is selected from hydrogen, and a $C_1$-$C_6$ alkyl group. In a further embodiment, $R_1$ and $R_2$ are each selected from hydrogen, methyl, ethyl, n-propyl, i-propyl, n-butyl, i-butyl, t-butyl, and combinations thereof.

In an embodiment, the silyl diol ester has the structure (III) wherein each of $R_1$-$R_6$ is selected from hydrogen, and a $C_1$-$C_6$ alkyl group. In a further embodiment, each of $R_1$ and $R_2$ is selected from hydrogen, methyl, ethyl, n-propyl, i-propyl, n-butyl, i-butyl, t-butyl, and combinations thereof, and $R_3$-$R_6$ are methyl. In another embodiment, each of $R_1$ and $R_2$ is selected from hydrogen, methyl, ethyl, n-propyl, i-propyl, n-butyl, i-butyl, t-butyl, and combinations thereof, $R_3$ and $R_5$ are methyl, and $R_4$ and $R_6$ are hydrogen.

The present disclosure provides a method for producing a silyl diol ester. In an embodiment, a method for producing a silyl diol ester includes reacting a carboxylate salt with a dialkyl silane of the structure (IV) below:

wherein $A_1$ and $A_2$ are the same or different and each is a halohydrocarbyl group having 1 to 20 carbon atoms. $R_3$ and $R_4$ are the same or different and each is selected from hydrogen and a hydrocarbyl group having 1 to 20 carbon atoms.

The method further includes forming a silyl diol ester. In an embodiment, the method includes forming a silyl diol ester of the structure (III) below.

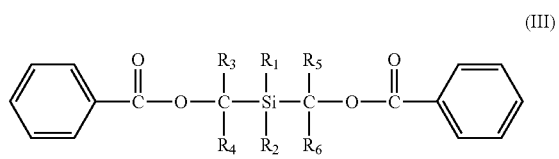

(III)

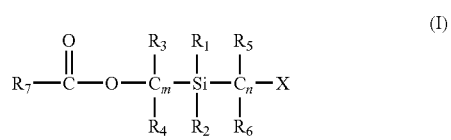

(I)

The substituents $R_1$-$R_6$ can be any substituent as disclosed for structure (III) above.

In an embodiment, a process for producing a procatalyst composition is provided. The process includes reacting a silyl ester, a procatalyst precursor, and a halogenating agent. The reaction occurs in a reaction mixture. The process further includes forming a procatalyst composition. The procatalyst composition includes a combination of a magnesium moiety, a titanium moiety, and an internal electron donor. The internal electron donor includes the silyl ester.

In an embodiment, another process for producing a procatalyst composition is provided. The process includes reacting 2,2-dimethyl-1,3-propylene glycol dibenzoate, a benzoate-containing magnesium precursor, and a halogenating agent. The reaction occurs in a reaction mixture. The process includes forming a procatalyst composition that includes a combination of a magnesium moiety, a titanium moiety and an internal electron donor. The internal electron donor includes ethyl benzoate and 2,2-dimethyl-1,3-propylene glycol dibenzoate.

In an embodiment, a procatalyst composition is provided. The procatalyst composition includes a combination of a magnesium moiety, a titanium moiety, and an internal electron donor. The internal electron donor includes a silyl ester. The silyl ester may have the structure (I), (II), or (III).

In an embodiment, a catalyst composition is provided. The catalyst composition includes a silyl ester. The catalyst composition also includes a cocatalyst. The catalyst composition may optionally include an external electron donor and/or an activity limiting agent.

In an embodiment, a process for producing an olefin-based polymer is provided. The process includes contacting, under polymerization conditions, at least one olefin with a catalyst composition. The catalyst composition includes a silyl ester. The process also includes forming an olefin-based polymer.

An advantage of the present disclosure is the provision of an improved procatalyst composition.

An advantage of the present disclosure is the provision of an improved catalyst composition.

An advantage of the present disclosure is the provision of a silyl ester suitable for use as an internal electron donor.

An advantage of the present disclosure is the provision of a silyl diol ester, suitable for use as an internal electron donor.

An advantage of the present disclosure is the provision of a procatalyst composition having a silyl ester and/or a silyl diol ester that produces olefin-based polymers with improved properties.

An advantage of the present disclosure is the provision of a catalyst composition having a silyl ester and/or a silyl diol ester that produces an olefin-based polymer with broad molecular weight distribution, and/or improved flexural modulus, and/or high isotacticity.

DETAILED DESCRIPTION

In an embodiment, the present disclosure is directed to a silyl ester compound with the structure (I) below.

The letters "m" and "n" are each an integer from 1 to 5, m and n being the same or different, m and n each denoting the number of carbon atoms in the respective carbon chain. It is understood that each additional carbon in the $C_m$ carbon chain and/or the $C_n$ carbon chain can include one or more R' substituent(s). The R' substituent(s) can be hydrogen or a substituted/unsubstituted hydrocarbyl group having 1 to 20 carbon atoms.

The substituents $R_1$, $R_2$, $R_3$, $R_4$, $R_5$, $R_6$ and $R_7$ can be the same or different. $R_1$-$R_7$ are selected from hydrogen, a substituted hydrocarbyl group having 1 to 20 carbon atoms, an unsubstituted hydrocarbyl group having 1 to 20 carbon atoms, and combinations thereof. As used herein, the term "hydrocarbyl" and "hydrocarbon" refer to substituents containing only hydrogen and carbon atoms, including branched or unbranched, saturated or unsaturated, cyclic, polycyclic or acyclic species, and combinations thereof. Nonlimiting examples of hydrocarbyl groups include alkyl-, cycloalkyl-, alkenyl-, alkadienyl-, cycloalkenyl-, cycloalkadienyl-, aryl-, aralkyl, alkylaryl, and alkynyl-groups.

As used herein, the terms "substituted hydrocarbyl" and "substituted hydrocarbon" refer to a hydrocarbyl group that is substituted with one or more nonhydrocarbyl substituent groups. A nonlimiting example of a nonhydrocarbyl substituent group is a heteroatom. As used herein, a "heteroatom" refers to an atom other than carbon or hydrogen. The heteroatom can be a non-carbon atom from Groups IV, V, VI, and VII of the Periodic Table. Nonlimiting examples of heteroatoms include: F, Cl, Br, N, O, P, B, S, and Si. As used herein, the term "halohydrocarbyl" refers to a hydrocarbyl that is substituted with one or more halogen atoms.

The symbol "X" of structure (I) represents an electron donating group. The term "electron donating group" refers to a functional group that is capable of donating one or more electron pairs to metal atom(s). Nonlimiting examples of suitable electron donating groups include —C(=O)OR, —O(O=)CR, —O(O=)CNHR, —(O=)CNRR', —NH(O=)CR, —NR'(O=)CR, —C(=O)R, —OR, —NHR, —NR'R, —SR, —OP(OR')(OR), —S(=O)R, —S(=O)$_2$R, —OS(=O)$_2$(OR), and combinations thereof. R and R' of electron donating group X can be a substituted or unsubstituted hydrocarbyl group having 1 to 20 carbon atoms.

The structure for each of the foregoing electron donating groups is provided in Table 1 below.

TABLE 1

| Abbreviation | Structure |
| --- | --- |
| —C(=O)OR | —C(=O)—OR |
| —O(O=)CR | —O—C(=O)—R |
| —(O=)CNHR | —C(=O)—N(H)—R |

TABLE 1-continued

| Abbreviation | Structure |
|---|---|
| —O(O=)CNRR' | (structure) |
| —NH(O=)CR | (structure) |
| —NR'(O=)CR | (structure) |
| —C(=O)R | (structure) |
| —OR | —O—R |
| —NHR | (structure) |
| —NR'R | (structure) |
| —SR | —S—R |
| —OP(OR')(OR) | (structure) |
| —S(=O)R | (structure) |
| —S(=O)$_2$R | (structure) |
| —OS(=O)$_2$(OR) | (structure) |

In an embodiment, the silyl ester includes $R_7$ that is a benzene-ring-containing group. As used herein, a "benzene-ring-containing group" is a component that includes one or more benzene rings. Nonlimiting examples of suitable benzene-ring-containing groups include single benzene groups such as phenyl groups, and multiple and/or fused benzene groups such as naphthyl groups. The benzene-ring-containing group may optionally be substituted with one or more of the following: $C_{1-20}$ alkyl group(s), $C_{1-20}$ alkoxy group(s), $C_{1-20}$alkoxycarbonyl group(s), halogen atom(s), and any combination thereof.

In an embodiment, the silyl ester includes $R_7$ that is a phenyl group. $R_1$ and $R_2$ are the same or different, $R_1$ and $R_2$ are each selected from hydrogen, a $C_{1-6}$ alkyl group, and combinations thereof. Nonlimiting examples of $C_1$-$C_6$ alkyl groups include methyl, ethyl, n-propyl, isopropyl, i-butyl, n-butyl, t-butyl, n-pentyl, and n-hexyl groups.

In an embodiment, the silyl ester includes $R_7$ that is a phenyl group, $R_3$-$R_6$ are hydrogen, and $R_1$ and $R_2$ are the same or different and each is selected from hydrogen, a $C_{1-6}$ alkyl group, and combinations thereof.

In an embodiment, the present disclosure provides a silyl diol ester. The silyl diol ester has the structure (II):

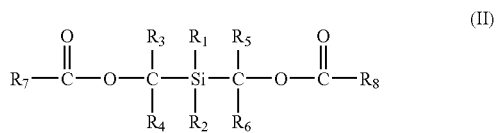

(II)

wherein $R_1$-$R_8$ are the same or different. Each of $R_1$-$R_8$ is selected from hydrogen, a substituted hydrocarbyl group having 1 to 20 carbon atoms, an unsubstituted hydrocarbyl group having 1 to 20 carbon atoms, and combinations thereof.

In an embodiment, $R_7$ and $R_8$ can be the same or different. Each of $R_7$ and $R_8$ is selected from a benzene-ring-containing group. The benzene-ring-containing group may optionally be substituted with one or more of the following: $C_{1-20}$ alkyl group(s), $C_{1-20}$ alkoxy group(s), $C_{1-20}$ alkoxycarbonyl group(s), halogen atom(s), and any combination thereof.

In an embodiment, $R_1$ and $R_2$ can be the same or different. Each of $R_1$ and $R_2$ is selected from hydrogen, a $C_1$-$C_6$ alkyl group, and combinations thereof.

In an embodiment, $R_7$ and $R_8$ are each a phenyl group. $R_1$-$R_6$ are the same or different and each is selected from hydrogen, a $C_1$-$C_6$ alkyl group, and combinations thereof.

In an embodiment, the silyl diol ester has the structure (III) below:

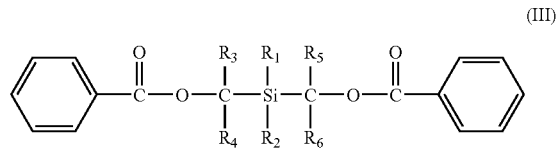

(III)

wherein $R_1$-$R_6$ are the same or different and each is selected from hydrogen, a $C_1$-$C_6$ alkyl group, and combinations thereof.

In an embodiment, the silyl diol ester of structure (III) includes $R_1$ and $R_2$ which are the same or different and each is selected from hydrogen, or a $C_1$-$C_6$ alkyl group. Each of $R_3$-$R_6$ is hydrogen.

In an embodiment, the silyl diol ester of structure (III) includes $R_1$ and $R_2$ that are the same or different. Each of $R_1$ and $R_2$ is selected from hydrogen, methyl, ethyl, n-propyl, i-propyl, n-butyl, i-butyl, t-butyl, and combinations thereof. Each of $R_3$-$R_6$ is hydrogen.

In an embodiment, the silyl diol ester of structure (III) includes $R_1$ and $R_2$ that are the same or different. Each of $R_1$ and $R_2$ is selected from hydrogen, methyl, ethyl, n-propyl, i-propyl, n-butyl, i-butyl, t-butyl, and combinations thereof. Each of $R_3$-$R_6$ is methyl.

In an embodiment, the silyl diol ester of structure (III) includes $R_1$ and $R_2$ that are the same or different. Each of $R_1$ and $R_2$ is selected from hydrogen, methyl, ethyl, n-propyl, i-propyl, n-butyl, i-butyl, t-butyl, and combinations thereof. Each of $R_3$ and $R_5$ is methyl. Each of $R_4$ and $R_6$ is hydrogen.

Nonlimiting examples of the silyl diol ester are set forth in Table 2 below.

TABLE 2

| Name | Structure |
|---|---|
| Bis(benzoyloxy)dimethylsilane | 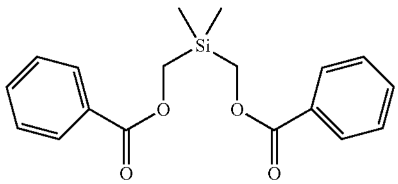 |
| Bis(benzoyloxy)diethylsilane | 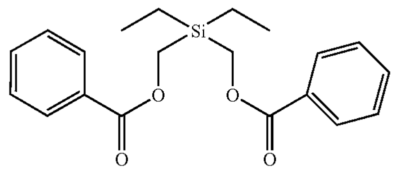 |
| Bis(benzoyloxy)ethylmethylsilane | 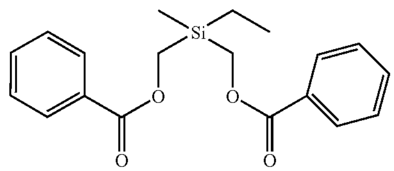 |
| Bis(benzoyloxy)isobutylmethylsilane | 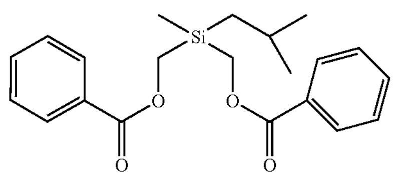 |

In an embodiment, a method for producing a silyl diol ester is provided. The method includes reacting a carboxylate salt with the dialkyl silane of a structure (IV) as described below.

(IV)

wherein $A_1$ and $A_2$ are the same or different and each is a halohydrocarbyl group having 1 to 20 carbon atoms. $A_3$ and $A_4$ are the same or different and each is selected from hydrogen and a hydrocarbyl group having 1 to 20 carbon atoms.

The reaction between the carboxylate salt and the dialkyl silane of the structure (IV) forms a silyl diol ester. The carboxylate salt can be a sodium carboxylate or a potassium carboxylate. In an embodiment, the carboxylate salt is potassium benzoate.

In an embodiment, the method includes forming a silyl diol ester of the structure (III) below:

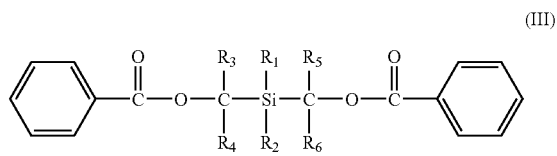

(III)

wherein $R_3$-$R_6$ are hydrogen, $R_1$ and $R_2$ are the same or different and each is selected from hydrogen, methyl, ethyl, n-propyl, i-propyl, n-butyl, i-butyl, t-butyl, and combinations thereof. Nonlimiting examples of silyl diol esters formed by the present method are found in Table 2.

An advantage of the foregoing silyl ester and silyl diol ester compounds is that they may be incorporated into procatalyst compositions and/or catalyst compositions in order to produce olefin-based polymers with improved properties.

The silyl ester may comprise two or more embodiments disclosed herein.

In an embodiment, a process for producing a procatalyst composition is provided. The process includes reacting a silyl ester, a procatalyst precursor and a halogenating agent. The reaction may occur in a reaction mixture. The process includes forming a procatalyst composition. The procatalyst composition includes a magnesium moiety, a titanium moiety, and an internal electron donor. The internal electron donor includes the silyl ester.

The procatalyst precursor can include (i) magnesium; (ii) a transition metal compound of an element from Periodic Table groups IV to VIII; (iii) a halide, an oxyhalide, and/or an alkoxide of (i) and/or (ii); and (iv) combinations of (i), (ii), and (iii). Nonlimiting examples of suitable procatalyst precursors include halides, oxyhalides, and alkoxides of magnesium, manganese, titanium, vanadium, chromium, molybdenum, zirconium, hafnium, and combinations thereof.

Various methods of making procatalyst precursors are known in the art. These methods are described, inter alia, in U.S. Pat. Nos. 6,825,146, 5,034,361; 5,082,907; 5,151,399; 5,229,342; 5,106,806; 5,146,028; 5,066,737; 5,077,357; 4,442,276; 4,540,679; 4,547,476; 4,460,701; 4816,433; 4,829,037; 4,927,797; 4,990,479; 5,066,738; 5,028,671; 5,153,158; 5,247,031; 5,247,032, and elsewhere. In an embodiment, the preparation of the procatalyst precursor involves halogenation of mixed magnesium and titanium alkoxides, and may involve the use of one or more compounds, referred to as "clipping agents", that aid in forming specific, low molecular weight, compositions of the desired morphology. Nonlimiting examples of suitable clipping agents include trialkylborates, especially triethylborate, phenolic compounds, especially cresol, and silanes.

In an embodiment, the procatalyst precursor is a magnesium moiety compound (MagMo), a mixed magnesium titanium compound (MagTi), or a benzoate-containing magnesium chloride compound (BenMag). In an embodiment, the procatalyst precursor is a magnesium moiety ("MagMo") precursor. The MagMo precursor contains magnesium as the sole metal component. The "MagMo precursor" includes a magnesium moiety. Nonlimiting examples of suitable magnesium moieties include anhydrous magnesium chloride and/or its alcohol adduct, magnesium alkoxide or aryloxide, mixed magnesium alkoxy halide, and/or carboxylated magnesium dialkoxide or aryloxide. In one embodiment, the MagMo precursor is a magnesium di($C_{1-4}$)alkoxide. In a further embodiment, the MagMo precursor is diethoxymagnesium.

In an embodiment, the procatalyst precursor is a mixed magnesium/titanium compound ("MagTi"). The "MagTi precursor" has the formula $Mg_dTi(OR^e)_fX_g$ wherein $R^e$ is an aliphatic or aromatic hydrocarbon radical having 1 to 14 carbon atoms or COR' wherein R' is an aliphatic or aromatic hydrocarbon radical having 1 to 14 carbon atoms; each $OR^e$ group is the same or different; X is independently chlorine, bromine or iodine, preferably chlorine; d is 0.5 to 56, or 2 to 4; f is 2 to 116 or 5 to 15; and g is 0.5 to 116, or 1 to 3. The precursors are prepared by controlled precipitation through removal of an alcohol from the reaction mixture used in their preparation. In an embodiment, a reaction medium comprises a mixture of an aromatic liquid, especially a chlorinated aromatic compound, most especially chlorobenzene, with an alkanol, especially ethanol. Suitable halogenating agents include titanium tetrabromide, titanium tetrachloride or titanium trichloride, especially titanium tetrachloride. Removal of the alkanol from the solution used in the halogenation, results in precipitation of the solid precursor, having especially desirable morphology and surface area. Moreover, the resulting precursors are particularly uniform in particle size.

In an embodiment, the procatalyst precursor is a benzoate-containing magnesium chloride material ("BenMag"). As used herein, a "benzoate-containing magnesium chloride" ("BenMag") may be a procatalyst (i.e., a halogenated procatalyst precursor) containing a benzoate internal electron donor. The BenMag material may also include a titanium moiety, such as a titanium halide. The benzoate internal electron donor is labile and can be replaced by other electron donors during procatalyst synthesis. Nonlimiting examples of suitable benzoate groups include ethyl benzoate, methyl benzoate, ethyl p-methoxybenzoate, methyl p-ethoxybenzoate, ethyl p-ethoxybenzoate, ethyl p-chlorobenzoate. In one embodiment, the benzoate group is ethyl benzoate. Not wishing to be bound by any particular theory, surprisingly and unexpectedly it has been found that the BenMag procatalyst precursor inhibits or otherwise prevents the silyl ester of the present procatalyst composition(s) from decomposing during preparation of the solid procatalyst composition. Nonlimiting examples of suitable BenMag procatalyst precursors include catalysts of the trade names SHAC™ 103 and SHAC™ 310 available from The Dow Chemical Company, Midland, Mich.

The present procatalyst composition also includes an internal electron donor. As used herein, an "internal electron donor" is a compound added during formation of the procatalyst composition that donates a pair of electrons to one or more metals present in the resultant procatalyst composition. Not bounded by any particular theory, it is believed that the internal electron donor assists in regulating the formation of active sites thereby enhancing catalyst stereoselectivity. The internal electron donor is one or more of any of the silyl esters and/or the silyl diol esters of structures (I)-(III) as disclosed above.

In an embodiment, the magnesium to internal electron donor molar ratio is from about 100:1 to about 1:1, or from about 30:1 to about 2:1, or from about 15:1 to about 3:1.

In an embodiment, the procatalyst precursor is converted to a solid procatalyst by way of halogenation. Halogenation includes contacting the procatalyst precursor with a halogenating agent in the presence of the internal electron donor. These components form a reaction mixture. Halogenation converts the magnesium moiety present in the procatalyst precursor into a magnesium halide support upon which the titanium moiety (such as a titanium halide) is deposited. Not wishing to be bound by any particular theory, it is believed that during halogenation the internal electron donor (1) regulates the position of titanium on the magnesium-based support, (2) facilitates conversion of the magnesium and titanium moieties into respective halides and (3) regulates the crystallite size of the magnesium halide support during conversion. Thus, provision of the internal electron donor yields a procatalyst composition with stereoselectivity.

In an embodiment, the halogenating agent is a titanium halide having the formula Ti(OR$^e$)$_f$X$_h$ wherein R$^e$ and X are defined as above, f is an integer from 0 to 3; h is an integer from 1 to 4; and f+h is 4. In an embodiment, the halogenation agent is TiCl$_4$. In a further embodiment, the halogenation is conducted in a reaction mixture that includes a chlorinated or a non-chlorinated aromatic liquid, such as dichlorobenzene, o-chlorotoluene, chlorobenzene, benzene, toluene, or xylene.

In yet another embodiment, the halogenation is conducted by use of a mixture of halogenating agent and chlorinated aromatic liquid comprising from 40 to 60 volume percent halogenating agent, such as TiCl$_4$.

In an embodiment, the reaction mixture is heated during halogenation. The procatalyst precursor and halogenating agent are contacted initially at a temperature from 0° C. to 60° C., or from 20° C. to 30° C., and heating is commenced at a rate of 0.1 to 10.0° C./minute, or at a rate of 1.0 to 5.0° C./minute. The internal electron donor may be added later, after an initial contact period between the halogenating agent and procatalyst precursor. Temperatures for the halogenation are from 60° C. to 150° C. (or any value or subrange therebetween), or from 90° C. to 120° C. Halogenation may be continued in the substantial absence of the internal electron donor for a period from 5 to 60 minutes, or from 10 to 50 minutes.

The manner in which the procatalyst precursor, halogenating agent and internal electron donor are contacted may be varied. In an embodiment, the procatalyst precursor is first contacted with a mixture containing the halogenating agent and a chlorinated aromatic compound. The resulting mixture is stirred and may be heated if desired. Next, the internal electron donor is added to the same reaction mixture without isolating or recovering the precursor. The foregoing process may be conducted in a single reactor with addition of the various ingredients controlled by automated process control.

Contact times of the procatalyst precursor with the internal electron donor are at least 10 minutes, or at least 15 minutes, or at least 20 minutes, or at least 1 hour at a temperature from at least 25° C., or at least 50° C., or at least 60° C. up to a temperature of 150° C., or up to 120° C., or up to 115° C., or up to 110° C.

The halogenation procedure may be repeated one, two, three, or more times as desired. In an embodiment, the resulting solid material is recovered from the reaction mixture and contacted one or more times in the absence (or in the presence) of the same (or different) internal electron donor components with a mixture of the halogenating agent in the chlorinated aromatic compound for at least about 10 minutes, or at least about 15 minutes, or at least about 20 minutes, and up to about 1 hour, or up to about 45 minutes, or up to about 30 minutes, at a temperature from at least about 25° C., or at least about 50° C., or at least about 60° C., to a temperature up to about 150° C., or up to about 120° C., or up to about 115° C.

After the foregoing halogenation procedure, the resulting solid procatalyst composition is separated from the reaction medium employed in the final process, by filtering for example, to produce a moist filter cake. The moist filter cake may then be rinsed or washed with a liquid diluent to remove unreacted TiCl$_4$ and may be dried to remove residual liquid, if desired. Typically the resultant solid procatalyst composition is washed one or more times with a "wash liquid," which is a liquid hydrocarbon such as an aliphatic hydrocarbon such as isopentane, isooctane, isohexane, hexane, pentane, or octane. The solid procatalyst composition then can be separated and dried or slurried in a hydrocarbon, especially a relatively heavy hydrocarbon such as mineral oil for further storage or use.

In an embodiment, the resulting solid procatalyst composition has a titanium content of from about 0.1 percent by weight to about 6.0 percent by weight, based on the total solids weight, or from about 1.0 percent by weight to about 4.5 percent by weight, or from about 1.5 percent by weight to about 3.5 percent by weight. In an embodiment, the internal electron donor may be present in the procatalyst composition in a molar ratio of internal electron donor to magnesium of from about 0.005:1 to about 1:1, or from about 0.01:1 to about 0.4:1. Weight percent is based on the total weight of the procatalyst composition.

In an embodiment, the procatalyst composition may be further treated by one or more of the following procedures prior to or after isolation of the solid procatalyst composition. The solid procatalyst composition may be contacted (halogenated) with a further quantity of titanium halide compound, if desired; it may be exchanged under metathesis conditions with an acid chloride, such as phthaloyl dichloride or benzoyl chloride; and it may be rinsed or washed, heat treated; or aged. The foregoing additional procedures may be combined in any order or employed separately, or not at all.

Not wishing to be bound by any particular theory, it is believed that (1) further halogenation by contacting the previously formed procatalyst composition with a titanium halide compound, especially a solution thereof in a halohydrocarbon diluent, and/or (2) further washing the previously formed procatalyst composition with a halohydrocarbon or hydrocarbon at an elevated temperature (100-150° C.), results in desirable modification of the procatalyst composition, possibly by removal of certain inactive metal compounds that are soluble in the foregoing diluent. Accordingly, in an embodiment, the procatalyst is contacted with a halogenating agent, such as a mixture of a titanium halide and a halohydrocarbon diluent, such as $TiCl_4$ and chlorobenzene, one or more times prior to isolation or recovery. In another embodiment, the procatalyst is washed at a temperature between 100 to 150° C. with chlorobenzene or o-chlorotoluene one or more times prior to isolation or recovery.

In an embodiment, a process for producing another procatalyst composition is provided. The process includes reacting 2,2-dimenthyl-1,3-propylene glycol dibenzoate, a benzoate containing magnesium chloride procatalyst precursor (BenMag), and a halogenating agent. The reaction may occur in a reaction mixture. The process includes forming a procatalyst composition. Formation of the procatalyst composition may occur by way of halogenation as previously disclosed. The procatalyst composition includes a combination of a magnesium moiety, a titanium moiety, and an internal electron donor. The internal electron donor includes ethyl benzoate and 2,2 dimethyl-1,3-propylene glycol dibenzoate.

Either process for producing a procatalyst composition may comprise two or more embodiments disclosed herein.

In an embodiment, a procatalyst composition is provided which includes a combination of a magnesium moiety, a titanium moiety, and an internal electron donor. The internal electron donor includes a silyl ester. The procatalyst composition is produced by way of the foregoing halogenation procedure that converts the procatalyst precursor and the internal electron donor into a combination of a magnesium moiety, a titanium moiety into which the internal electron donor is incorporated. The internal electron donor may be any silyl ester as disclosed herein. The procatalyst precursor from which the procatalyst composition is formed can be the magnesium moiety precursor, the mixed magnesium/titanium precursor, or the benzoate-containing magnesium chloride precursor.

In an embodiment, the magnesium moiety is a magnesium halide. In another embodiment, the magnesium halide is magnesium chloride, or magnesium chloride alcohol adduct.

In an embodiment, the titanium moiety is a titanium chloride. In another embodiment the titanium halide is titanium tetrachloride.

In an embodiment, the procatalyst composition is a combination of a magnesium chloride, a titanium chloride and the internal electron donor. In another embodiment, the procatalyst composition includes a magnesium chloride support upon which a titanium chloride is deposited and into which the internal electron donor is incorporated.

In an embodiment, the procatalyst composition includes from about 0.1 wt % to about 20 wt % silyl ester. The weight percent is based on the total weight to the procatalyst composition.

In an embodiment, the internal electron donor of the procatalyst composition is a silyl ester that has the structure (I):

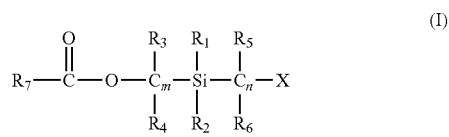

(I)

wherein m and n are the same or different, m and n are each an integer from 1 to 5 denoting a hydrocarbyl with the same number of carbon atoms. $R_1$-$R_7$ are the same or different and each is selected from hydrogen, a substituted hydrocarbyl group having 1 to 20 carbon atoms, an unsubstituted hydrocarbyl group having 1 to 20 carbon atoms, and combinations thereof. X is an electron donating group as previously disclosed for structure (I). The internal electron donor may comprise one or more embodiments of structure (I) as previously disclosed.

In an embodiment, $R_7$ is selected from a benzene-ring-containing group. The benzene-ring-containing group may be optionally substituted with one or more of the following: $C_{1-20}$ alkyl group(s), $C_{1-20}$ alkoxy group(s), $C_{1-20}$ alkoxycarbonyl group(s), halogen atom(s), and any combination thereof.

In an embodiment, the catalyst composition includes an internal electron donor with the structure (II) below:

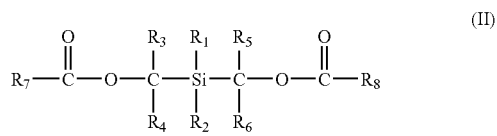

(II)

wherein $R_1$-$R_8$ are the same or different. Each of $R_1$-$R_8$ is selected from the substituents set forth for structure (II) above. In an embodiment, $R_7$ and $R_8$ are the same or different. Each of $R_7$ and $R_8$ is selected from a benzene-ring-containing group which may be optionally substituted with one or more of the following: a $C_{1-20}$ alkyl group, a $C_{1-20}$ alkoxy group, a $C_{1-20}$ alkoxycarbonyl group, a halogen atom, and any combination thereof. The internal electron donor may comprise one or more embodiments of structure (II) as previously disclosed.

In an embodiment, the procatalyst composition includes an internal electron donor with the structure (III) as follows:

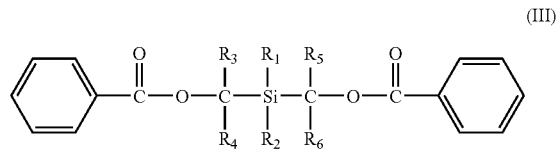

(III)

wherein $R_1$-$R_6$ are the same or different and each is selected from substituents set forth for structure (III) above.

The internal electron donor may comprise one or more embodiments of structure (III) as previously disclosed.

In an embodiment, each of $R_3$-$R_6$ is hydrogen, $R_1$ and $R_2$ are the same or different and each is selected from hydrogen, a $C_1$-$C_6$ alkyl group, and combinations thereof. In a further embodiment, each of $R_1$ and $R_2$ is selected from methyl, ethyl, n-propyl, i-propyl, n-butyl, i-butyl, t-butyl, and combinations thereof.

In an embodiment, the silyl diol ester of structure (III) includes $R_1$ and $R_2$ that are the same or different. Each of $R_1$ and $R_2$ is selected from hydrogen, methyl, ethyl, n-propyl, i-propyl, n-butyl, i-butyl, t-butyl, and combinations thereof. Each of $R_3$-$R_6$ is methyl.

In an embodiment, the silyl diol ester of structure (III) includes $R_1$ and $R_2$ that are the same or different. Each of $R_1$ and $R_2$ is selected from hydrogen, methyl, ethyl, n-propyl, i-propyl, n-butyl, i-butyl, t-butyl, and combinations thereof. Each of $R_3$ and $R_5$ is methyl. Each of $R_4$ and $R_6$ is hydrogen.

In an embodiment, the procatalyst composition includes an internal electron donor that is selected from bis(benzoyloxy) dimethylsilane, bis(benzoyloxy)diethylsilane, bis(benzoyloxy)ethylmethylsilane, bis(benzoyloxy)isobutylmethylsilane, and combinations thereof.

The procatalyst composition may comprise two or more embodiments disclosed herein.

In an embodiment, a catalyst composition is provided. As used herein, a "catalyst composition" is a composition that forms an olefin-based polymer when contacted with an olefin under polymerization conditions. The catalyst composition includes a procatalyst composition and a cocatalyst. The procatalyst composition includes a silyl ester. The silyl ester can be any silyl ester or silyl diol ester as disclosed herein. The catalyst composition may contain any procatalyst composition as disclosed herein. The catalyst composition may optionally include an external electron donor and/or an activity limiting agent.

The catalyst composition includes a cocatalyst. As used herein, a "cocatalyst" is a substance capable of converting the procatalyst composition to an active polymerization catalyst. The cocatalyst may include hydrides, alkyls, or aryls of aluminum, lithium, zinc, tin, cadmium, beryllium, magnesium, and combinations thereof. In an embodiment, the cocatalyst is a hydrocarbyl aluminum cocatalyst represented by the formula $R_3Al$ wherein each R is an alkyl, cycloalkyl, aryl, or hydride radical; at least one R is a hydrocarbyl radical; two or three R radicals can be joined in a cyclic radical forming a heterocyclic structure; each R can be the same or different; and each R, which is a hydrocarbyl radical, has 1 to 20 carbon atoms, and preferably 1 to 10 carbon atoms. In a further embodiment, each alkyl radical can be straight or branched chain and such hydrocarbyl radical can be a mixed radical, i.e., the radical can contain alkyl, aryl, and/or cycloalkyl groups. Nonlimiting examples of suitable radicals are: methyl, ethyl, n-propyl, i-propyl, n-butyl, i-butyl, t-butyl, n-pentyl, neopentyl, n-hexyl, 2-methylpentyl, n-heptyl, n-octyl, isooctyl, 2-ethylhexyl, 5,5-dimethylhexyl, n-nonyl, n-decyl, isodecyl, n-undecyl, n-dodecyl, phenyl, phenethyl, methoxyphenyl, benzyl, tolyl, xylyl, naphthyl, methylnapthyl, cyclohexyl, cycloheptyl, and cyclooctyl.

Nonlimiting examples of suitable hydrocarbyl aluminum compounds are as follows: triisobutylaluminum, trihexylaluminum, diisobutylaluminum hydride, dihexylaluminum hydride, isobutylaluminum dihydride, hexylaluminum dihydride, di-isobutylhexylaluminum, isobutyl dihexylaluminum, trimethylaluminum, triethylaluminum, tripropylaluminum, triisopropylaluminum, tri-n-butylaluminum, trioctylaluminum, tridecylaluminum, tridodecylaluminum, tribenzylaluminum, triphenylaluminum, trinaphthylaluminum, and tritolylaluminum. In an embodiment, the cocatalyst is selected from triethylaluminum, triisobutylaluminum, trihexylaluminum, di-isobutylaluminum hydride, and dihexylaluminum hydride.

In an embodiment, the cocatalyst is a hydrocarbyl aluminum compound represented by the formula $R_nAlX_{3-n}$ wherein n=1 or 2, R is an alkyl, and X is a halide or alkoxide. Nonlimiting examples of suitable compounds are as follows: methylaluminoxane, isobutylaluminoxane, diethylaluminum ethoxide, diisobutylaluminum chloride, tetraethyldialuminoxane, tetraisobutyldialuminoxane, diethylaluminum chloride, ethylaluminum dichloride, methylaluminum dichloride, and dimethylaluminum chloride.

In an embodiment, the cocatalyst is triethylaluminum. The molar ratio of aluminum to titanium is from about 5:1 to about 500:1, or from about 10:1 to about 200:1, or from about 15:1 to about 150:1, or from about 20:1 to about 100:1. In another embodiment, the molar ratio of aluminum to titanium is about 45:1.

In an embodiment, the catalyst composition includes an external electron donor. As used herein, an "external electron donor" is a compound added independent of procatalyst formation and contains at least one functional group that is capable of donating a pair of electrons to a metal atom. Bounded by no particular theory, it is believed that the external electron donor enhances catalyst stereoselectivity, (i.e., reduces xylene soluble material in the formant polymer).

In an embodiment, the external electron donor may be selected from one or more of the following: an alkoxysilane, an amine, an ether, a carboxylate, a ketone, an amide, a carbamate, a phosphine, a phosphate, a phosphite, a sulfonate, a sulfone, and/or a sulfoxide.

In an embodiment, the external electron donor is an alkoxysilane. The alkoxysilane has the general formula: $SiR_m(OR')_{4-m}$ (I) where R independently each occurrence is hydrogen or a hydrocarbyl or an amino group optionally substituted with one or more substituents containing one or more Group 14, 15, 16, or 17 heteroatoms, said R containing up to 20 atoms not counting hydrogen and halogen; R' is a $C_{1-20}$ alkyl group; and m is 0, 1, 2 or 3. In an embodiment, R is $C_{6-12}$ alkylaryl or aralkyl, $C_{3-12}$ cycloalkyl, $C_{1-12}$ alkyl, $C_{3-12}$ branched alkyl, or $C_{3-12}$ cyclic or acyclic amino group, R is $C_{1-4}$ alkyl, and m is 1 or 2. Nonlimiting examples of suitable silane compositions include dicyclopentyldimethoxysilane, di-tert-butyldimethoxysilane, methylcyclohexyldimethoxysilane, methylcyclohexyldiethoxysilane, ethylcyclohexyldimethoxysilane, diphenyldimethoxysilane, diisopropyldimethoxysilane, di-n-propyldimethoxysilane, diisobutyldimethoxysilane, diisobutyldiethoxysilane, isobutylisopropyldimethoxysilane, di-n-butyldimethoxysilane, cyclopentyltrimethoxysilane, isopropyltrimethoxysilane, n-propyltrimethoxysilane, n-propyltriethoxysilane, ethyltriethoxysilane, tetramethoxysilane, tetraethoxysilane, diethylaminotriethoxysilane, cyclopentylpyrrolidinodimethoxysilane, bis(pyrrolidino)dimethoxysilane, bis(perhydroisoquinolino)dimethoxysilane, and dimethyldimethoxysilane. In an embodiment, the silane composition is dicyclopentyldimethoxysilane (DCPDMS), methylcyclohexyldimethoxysilane (MChDMS), or n-propyltrimethoxysilane (NPTMS), and any combination of thereof.

In one embodiment, the external electron donor is dicyclopentyldimethoxysilane. In another embodiment, the external electron donor is n-propyltrimethoxysilane.

In an embodiment, the external electron donor can be a mixture of at least two alkoxysilanes. In a further embodiment, the mixture can be dicyclopentyldimethoxysilane and one or more of the following: methylcyclohexyldiethoxysilane, di-n-butyldimethoxysilane, diisobutyldiethoxysilane, n-propyltriethoxysilane, ethyltriethoxysilane, tetramethoxysilane, tetraethoxysilane, and combinations thereof.

In an embodiment, the external electron donor is selected from one or more of the following: a benzoate, a succinate, or and/or a diol ester. In an embodiment, the external donor is 2,2,6,6-tetramethylpiperidine. In another embodiment, the external electron donor is a diether.

In an embodiment, the catalyst composition includes an activity limiting agent (ALA). As used herein, an "activity limiting agent" ("ALA") is a material that reduces catalyst activity at elevated temperature (i.e., temperature greater than about 85° C.). An ALA inhibits or otherwise prevents polymerization reactor upset and ensures continuity of the polymerization process. Typically, the activity of Ziegler-Natta catalysts increases as the reactor temperature rises. Ziegler-Natta catalysts also typically maintain high activity near the softening point temperature of the polymer produced. The heat generated by the exothermic polymerization reaction may cause polymer particles to form agglomerates and may ultimately lead to disruption of continuity for the polymer production process. The ALA reduces catalyst activity at elevated temperature, thereby preventing reactor upset, reducing (or preventing) particle agglomeration, and ensuring continuity of the polymerization process.

The activity limiting agent may be a carboxylic acid ester, a diether, a diol ester, a poly(alkene glycol), and combinations thereof. The carboxylic acid ester can be an aliphatic or aromatic, mono- or poly-carboxylic acid ester. Nonlimiting examples of suitable monocarboxylic acid esters include ethyl and methyl benzoate, ethyl p-methoxybenzoate, methyl p-ethoxybenzoate, ethyl p-ethoxybenzoate, ethyl acrylate, methyl methacrylate, ethyl acetate, ethyl p-chlorobenzoate, hexyl p-aminobenzoate, isopropyl naphthenate, n-amyl toluate, ethyl cyclohexanoate and propyl pivalate.

Nonlimiting examples of suitable polycarboxylic acid esters include dimethyl phthalate, diethyl phthalate, di-n-propyl phthalate, diisopropyl phthalate, di-n-butyl phthalate, diisobutyl phthalate, di-tert-butyl phthalate, diisoamyl phthalate, di-tert-amyl phthalate, dineopentyl phthalate, di-2-ethylhexyl phthalate, and di-2-ethyldecyl phthalate.

The aliphatic carboxylic acid ester may be a $C_4$-$C_{30}$ aliphatic acid ester, may be a mono- or a poly- (two or more) ester, may be straight chain or branched, may be saturated or unsaturated, and any combination thereof. The $C_4$-$C_{30}$ aliphatic acid ester may also be substituted with one or more Group 14, 15 or 16 heteroatom containing substituents. Nonlimiting examples of suitable $C_4$-$C_{30}$ aliphatic acid esters include $C_{1-20}$ alkyl esters of aliphatic $C_{4-30}$ monocarboxylic acids, $C_{1-20}$ alkyl esters of aliphatic $C_{8-20}$ monocarboxylic acids, $C_{1-4}$ alkyl mono- and diesters of aliphatic $C_{4-20}$ monocarboxylic acids and dicarboxylic acids, $C_{1-4}$ alkyl esters of aliphatic $C_{8-20}$ monocarboxylic acids and dicarboxylic acids, and $C_{4-20}$ mono- or polycarboxylate derivatives of $C_{2-100}$ (poly)glycols or $C_{2-100}$ (poly)glycol ethers. In a further embodiment, the $C_4$-$C_{30}$ aliphatic acid ester may be a myristate, a sebacate, (poly)(alkylene glycol) mono- or diacetates, (poly)(alkylene glycol) mono- or di-myristates, (poly)(alkylene glycol) mono- or di-laurates, (poly)(alkylene glycol) mono- or di-oleates, glyceryl tri(acetate), glyceryl tri-ester of $C_{2-40}$ aliphatic carboxylic acids, and mixtures thereof. In a further embodiment, the $C_4$-$C_{30}$ aliphatic ester is isopropyl myristate or di-n-butyl sebacate.

In an embodiment, the activity limiting agent includes a diether. The diether can be a dialkylether represented by the following structure (V):

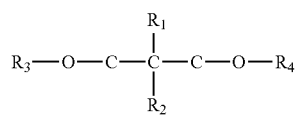

wherein $R_1$ to $R_4$ are independently of one another an alkyl, aryl or aralkyl group having up to 20 carbon atoms, which may optionally contain a group 14, 15, 16, or 17 heteroatom, and $R_1$ and $R_2$ may be a hydrogen atom. $R_1$ and $R_2$ may also be linked to form a cyclic structure, such as cyclopentadiene or fluorene. The dialkylether may be linear or branched, and may include one or more of the following groups: alkyl, cycloaliphatic, aryl, alkylaryl or arylalkyl radicals with 1-18 carbon atoms, and hydrogen.

In an embodiment, the activity limiting agent includes a succinate composition having the following structure (VI):

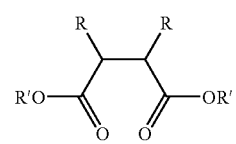

wherein R and R' may be the same or different, R and/or R' including one or more of the following groups: linear or branched alkyl, alkenyl, cycloalkyl, aryl, arylalkyl or alkylaryl group, optionally containing heteroatoms. One or more ring structures can be formed via one or both 2- and 3-position carbon atom.

In an embodiment, the activity limiting agent includes a diol ester as represented by the following structure (VII):

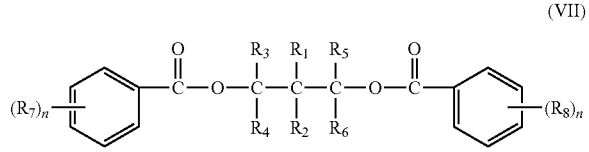

wherein n is an integer from 1 to 5. $R_1$ and $R_2$, may be the same or different, and each may be selected from hydrogen, methyl, ethyl, n-propyl, i-propyl, n-butyl, i-butyl, t-butyl, allyl, phenyl, or halophenyl group. $R_3$, $R_4$, $R_5$, $R_6$, $R_7$, and $R_8$, may be the same or different, and each may be selected from hydrogen, halogen, substituted, or unsubstituted hydrocarbyl having 1 to 20 carbon atoms. $R_1$-$R_6$ groups may optionally contain one or more heteroatoms replacing carbon, hydrogen or both, the hetero-atom selected from nitrogen, oxygen, sulfur, silicon, phosphorus and a halogen. Any of $R_1$-$R_6$ groups may be linked to form a cyclic structure. $R_7$ and $R_8$, may be the same or different, may be bonded to any carbon atom of the 2-, 3-, 4-, 5-, and 6-position of the phenyl ring.

In an embodiment, the external electron donor and activity limiting agent can be added into the reactor separately. In another embodiment, the external electron donor and the activity limiting agent can be mixed together in advance and then added into the reactor as a mixture. In the mixture, more than one external electron donor or more than one activity limiting agent can be used. In an embodiment, the mixture is dicyclopentyldimethoxysilane and isopropyl myristate, dicyclopentyldimethoxysilane and poly(ethylene glycol) laurate, dicyclopentyldimethoxysilane and isopropyl myristate and poly(ethylene glycol) dioleate, methylcyclohexyldimethoxysilane and isopropyl myristate, n-propyltrimethoxysilane and isopropyl myristate, dimethyldimethoxysilane and methylcyclohexyldimethoxysilane and isopropyl myristate, dicyclopentyldimethoxysilane and n-propyltriethoxysilane and isopropyl myristate, and dicyclopentyldimethoxysilane and tetraethoxysilane and isopropyl myristate and combinations thereof.

In an embodiment, the catalyst composition includes any of the foregoing external electron donors in combination with any of the foregoing activity limiting agents.

The present catalyst composition may comprise two or more embodiments disclosed herein.

In an embodiment, a process for producing an olefin-based polymer is provided. The process includes contacting at least one olefin with a catalyst composition under polymerization conditions. The catalyst composition includes a silyl ester. The silyl ester can be any silyl ester as disclosed herein. The process further includes forming an olefin-based polymer.

In an embodiment, the catalyst composition includes a procatalyst composition and a cocatalyst. The procatalyst composition may be any procatalyst composition as disclosed herein. Similarly, the cocatalyst may be any cocatalyst as disclosed herein. The catalyst composition may include an external electron donor and/or an activity limiting agent as previously disclosed.

In an embodiment, the olefin-based polymer can be a propylene-based olefin, an ethylene-based olefin, and combinations thereof. In an embodiment, the olefin-based polymer is a propylene-based polymer.

One or more olefin monomers can be introduced a polymerization reactor to react with the catalyst and to form a polymer (or a fluidized bed of polymer particles). Nonlimiting examples of suitable olefin monomers include ethylene, propylene, $C_{4-20}$ $\alpha$-olefins, such as 1-butene, 1-pentene, 1-hexene, 4-methyl-1-pentene, 1-heptene, 1-octene, 1-decene, 1-dodecene and the like; $C_{4-20}$ diolefins, such as 1,3-butadiene, 1,3-pentadiene, norbornadiene, 5-ethylidene-2-norbornene (ENB) and dicyclopentadiene; $C_{8-40}$ vinyl aromatic compounds including styrene, o-, m-, and p-methylstyrene, divinylbenzene, vinylbiphenyl, vinylnapthalene; and halogen-substituted $C_{8-40}$ vinyl aromatic compounds such as chlorostyrene and fluorostyrene.

As used herein, "polymerization conditions" are temperature and pressure parameters within a polymerization reactor suitable for promoting polymerization between the catalyst composition and an olefin to form the desired polymer. The polymerization process may be a gas phase, a slurry, or a bulk polymerization process, operating in one, or more than one, polymerization reactor.

In an embodiment, polymerization occurs by way of gas phase polymerization. As used herein, "gas phase polymerization" is the passage of an ascending fluidizing medium, the fluidizing medium containing one or more monomers, in the presence of a catalyst through a fluidized bed of polymer particles maintained in a fluidized state by the fluidizing medium. "Fluidization," "fluidized," or "fluidizing" is a gas-solid contacting process in which a bed of finely divided polymer particles is lifted and agitated by a rising stream of gas. Fluidization occurs in a bed of particulates when an upward flow of fluid through the interstices of the bed of particles attains a pressure differential and frictional resistance increment exceeding particulate weight. Thus, a "fluidized bed" is a plurality of polymer particles suspended in a fluidized state by a stream of a fluidizing medium. A "fluidizing medium" is one or more olefin gases, optionally a carrier gas (such as $H_2$ or $N_2$) and optionally a liquid (such as a hydrocarbon) which ascends through the gas-phase reactor.

A typical gas-phase polymerization reactor (or gas phase reactor) includes a vessel (i.e., the reactor), the fluidized bed, a distribution plate, inlet and outlet piping, a compressor, a cycle gas cooler or heat exchanger, and a product discharge system. The vessel includes a reaction zone and a velocity reduction zone, each of which is located above the distribution plate. The bed is located in the reaction zone. In an embodiment, the fluidizing medium includes propylene gas and at least one other gas such as an olefin and/or a carrier gas such as hydrogen or nitrogen.

In an embodiment, the contacting occurs by way of feeding the catalyst composition into the polymerization reactor and introducing the olefin into the polymerization reactor. In an embodiment, the process includes contacting the olefin with a cocatalyst. The cocatalyst can be mixed with the procatalyst composition (pre-mix) prior to the introduction of the procatalyst composition into the polymerization reactor. In another embodiment, cocatalyst is added to the polymerization reactor independently of the procatalyst composition. The independent introduction of the cocatalyst into the polymerization reactor can occur simultaneously, or substantially simultaneously, with the procatalyst composition feed.

In an embodiment, the process includes mixing the external electron donor (and optionally the activity limiting agent) with the procatalyst composition. The external electron donor can be complexed with the cocatalyst and mixed with the procatalyst composition (pre-mix) prior to contact between the catalyst composition and the olefin. In another embodiment, the external electron donor and/or the activity limiting agent can be added independently to the polymerization reactor. In an embodiment, the external electron donor is dicyclopentyldimethoxysilane or n-propyltrimethoxysilane.

In another embodiment, the catalyst composition includes dicyclopentyldimethoxysilane or n-propyltrimethoxysilane and an activity limiting agent such as isopropyl myristate.

In an embodiment, a polypropylene homopolymer is produced in a first reactor. The content of the first reactor is subsequently transferred to a second reactor into which ethylene is introduced. This results in production of a propylene-ethylene copolymer in the second reactor.

In an embodiment, a polypropylene homopolymer is formed via introduction of propylene and any of the present procatalyst compositions, cocatalysts, external electron donors, and activity limiting agents in the first reactor. The polypropylene homopolymer is introduced into the second reactor along with ethylene (and optionally propylene) and optionally an external electron donor and/or optionally an activity limiting agent. The external electron donor and the activity limiting agent may be the same as or different from the respective components used in the first reactor. This produces a propylene-ethylene copolymer (such as an impact copolymer) in the second reactor.

In an embodiment, the olefin is propylene. The process includes forming a propylene-based polymer having a melt flow rate (MFR) from about 0.01 g/10 min to about 800 g/10 min, or from about 0.1 g/10 min to about 200 g/10 min, or from about 0.5 g/10 min to about 150 g/10 min. In a further embodiment, the propylene-based polymer is a polypropylene homopolymer.

In an embodiment, the olefin is propylene. The process includes forming a propylene-based polymer having a xylene solubles content from about 0.5% to about 10%, or from about 1% to about 8%, or from about 1% to about 4%. In a further embodiment, the propylene-based polymer is a polypropylene homopolymer.

In an embodiment, the olefin is propylene. The process includes forming a propylene-based polymer having a polydispersity index (PDI) from about 4 to about 20, or from about 4 to about 20, or from about 5 to about 10, or from about 6 to about 8. In a further embodiment, the propylene-based polymer is a polypropylene homopolymer.

In an embodiment, the olefin is propylene. The process includes forming a propylene-based polymer having a flexural modulus from about 200 kpsi to about 400 kpsi, or from about 220 kpsi to about 390 kpsi, or from about 230 kpsi to about 350 kpsi, or from about 240 kpsi to about 320 kpsi. In a further embodiment, the propylene-based polymer is a polypropylene homopolymer.

The present process for producing an olefin-based polymer may comprise two or more embodiments disclosed herein.

Not wishing to be bound by any particular theory, it is believed that the present catalyst compositions with silyl ester and/or silyl diol ester internal electron donor yield olefin-based polymers with a broader molecular weight distribution when compared to procatalyst compositions with a similar procatalyst precursor and a conventional internal electron donor. For example, the present catalyst compositions produce propylene-based polymers with a broader PDI and a greater flexural modulus when compared to propylene-based polymers made from similar catalysts having a phthalate internal electron donor.

DEFINITIONS

All references to the Periodic Table of the Elements herein shall refer to the Periodic Table of the Elements, published and copyrighted by CRC Press, Inc., 2003. Also, any references to a Group or Groups shall be to the Groups or Groups reflected in this Periodic Table of the Elements using the IUPAC system for numbering groups. Unless stated to the contrary, implicit from the context, or customary in the art, all parts and percents are based on weight. For purposes of United States patent practice, the contents of any patent, patent application, or publication referenced herein are hereby incorporated by reference in their entirety (or the equivalent US version thereof is so incorporated by reference), especially with respect to the disclosure of synthetic techniques, definitions (to the extent not inconsistent with any definitions provided herein) and general knowledge in the art.

The term "comprising," and derivatives thereof, is not intended to exclude the presence of any additional component, step or procedure, whether or not the same is disclosed herein. In order to avoid any doubt, all compositions claimed herein through use of the term "comprising" may include any additional additive, adjuvant, or compound whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination.

Any numerical range recited herein, includes all values from the lower value to the upper value, in increments of one unit, provided that there is a separation of at least 2 units between any lower value and any higher value. As an example, if it is stated that the amount of a component, or a value of a compositional or a physical property, such as, for example, amount of a blend component, softening temperature, melt index, etc., is between 1 and 100, it is intended that all individual values, such as, 1, 2, 3, etc., and all subranges, such as, 1 to 20, 55 to 70, 197 to 100, etc., are expressly enumerated in this specification. For values which are less than one, one unit is considered to be 0.0001, 0.001, 0.01 or 0.1, as appropriate. These are only examples of what is specifically intended, and all possible combinations of numerical values between the lowest value and the highest value enumerated, are to be considered to be expressly stated in this application. In other words, any numerical range recited herein includes any value or subrange within the stated range. Numerical ranges have been recited, as discussed herein, reference melt index, melt flow rate, and other properties.

The terms "blend" or "polymer blend," as used herein, is a blend of two or more polymers. Such a blend may or may not be miscible (not phase separated at molecular level). Such a blend may or may not be phase separated. Such a blend may or may not contain one or more domain configurations, as determined from transmission electron spectroscopy, light scattering, x-ray scattering, and other methods known in the art.

The term "composition," as used herein, includes a mixture of materials which comprise the composition, as well as reaction products and decomposition products formed from the materials of the composition.

The term "polymer" is a macromolecular compound prepared by polymerizing monomers of the same or different type. "Polymer" includes homopolymers, copolymers, terpolymers, interpolymers, and so on. The term "interpolymer" means a polymer prepared by the polymerization of at least two types of monomers or comonomers. It includes, but is not limited to, copolymers (which usually refers to polymers prepared from two different types of monomers or comonomers, terpolymers (which usually refers to polymers prepared from three different types of monomers or comonomers), tetrapolymers (which usually refers to polymers prepared from four different types of monomers or comonomers), and the like.

The term "interpolymer," as used herein, refers to polymers prepared by the polymerization of at least two different types of monomers. The generic term interpolymer thus includes copolymers, usually employed to refer to polymers prepared from two different monomers, and polymers prepared from more than two different types of monomers.

The term "olefin-based polymer" is a polymer containing, in polymerized form, a majority weight percent of an olefin, for example ethylene or propylene, based on the total weight of the polymer. Nonlimiting examples of olefin-based polymers include ethylene-based polymers and propylene-based polymers.

The term, "ethylene-based polymer," as used herein, refers to a polymer that comprises a majority weight percent polymerized ethylene monomer (based on the total weight of polymerizable monomers), and optionally may comprise at least one polymerized comonomer.

The term, "ethylene/α-olefin interpolymer," as used herein, refers to an interpolymer that comprises a majority weight percent polymerized ethylene monomer (based on the total amount of polymerizable monomers), and at least one polymerized α-olefin.

The term, "propylene-based polymer," as used herein, refers to a polymer that comprises a majority weight percent polymerized propylene monomer (based on the total amount of polymerizable monomers), and optionally may comprise at least one polymerized comonomer.

The term "alkyl," as used herein, refers to a branched or unbranched, saturated or unsaturated acyclic hydrocarbon radical. Nonlimiting examples of suitable alkyl radicals include, for example, methyl, ethyl, n-propyl, i-propyl, 2-propenyl (or allyl), vinyl, n-butyl, t-butyl, i-butyl (or 2-methylpropyl), etc. The alkyls have 1 and 20 carbon atoms.

The term "substituted alkyl," as used herein, refers to an alkyl as just described in which one or more hydrogen atom bound to any carbon of the alkyl is replaced by another group such as a halogen, aryl, substituted aryl, cycloalkyl, substituted cycloalkyl, heterocycloalkyl, substituted heterocycloalkyl, halogen, haloalkyl, hydroxy, amino, phosphido, alkoxy, amino, thio, nitro, and combinations thereof. Suitable substituted alkyls include, for example, benzyl, trifluoromethyl and the like.

The term "aryl," as used herein, refers to an aromatic substituent which may be a single aromatic ring or multiple aromatic rings which are fused together, linked covalently, or linked to a common group such as a methylene or ethylene moiety. The aromatic ring(s) may include phenyl, naphthyl, anthracenyl, and biphenyl, among others. The aryls have 6 to 20 carbon atoms.

Test Methods

Flexural modulus is determined in accordance with ASTM D790-00.

Melt flow rate is measured in accordance with ASTM D 1238-01 test method at 230° with a 2.16 kg weight for propylene-based polymers.

Xylene Solubles (XS) is measured using a $^1$H NMR method as described in U.S. Pat. No. 5,539,309, the entire content of which is incorporated herein by reference.

Polydispersity Index (PDI) is measured by an AR-G2 rheometer which is a stress control dynamic spectrometer manufactured by TA Instruments using a method according to Zeichner G R, Patel P D (1981) "A comprehensive Study of Polypropylene Melt Rheology" Proc. of the $2^{nd}$ World Congress of Chemical Eng., Montreal, Canada. An ETC oven is used to control the temperature at 180° C.±0.1° C. Nitrogen is used to purge the inside of the oven to keep the sample from degradation by oxygen and moisture. A pair of 25 mm in diameter cone and plate sample holder is used. Samples are compress molded into 50 mm×100 mm×2 mm plaque. Samples are then cut into 19 mm square and loaded on the center of the bottom plate. The geometries of upper cone is (1) Cone angle: 5:42:20 (deg:min:sec); (2) Diameter: 25 mm; (3) Truncation gap: 149 micron. The geometry of the bottom plate is 25 mm cylinder.

Testing Procedure:
  The cone & plate sample holder are heated in the ETC oven at 180° C. for 2 hours. Then the gap is zeroed under blanket of nitrogen gas.
  Cone is raised to 2.5 mm and sample loaded unto the top of the bottom plate.
  Start timing for 2 minutes.
  The upper cone is immediately lowered to slightly rest on top of the sample by observing the normal force.
  After two minutes the sample is squeezed down to 165 micron gap by lower the upper cone.
  The normal force is observed. When the normal force is down to <0.05 Newton the excess sample is removed from the edge of the cone and plate sample holder by a spatula.
  The upper cone is lowered again to the truncation gap which is 149 micron.

An Oscillatory Frequency Sweep test is performed under these conditions:
  1. Test delayed at 180° C. for 5 minutes.
  ii. Frequencies: 628.3 r/s to 0.1 r/s.
  iii. Data acquisition rate: 5 point/decade.
  iv. Strain: 10%

When the test is completed the crossover modulus (Gc) is detected by the Rheology Advantage Data Analysis program furnished by TA Instruments.

PDI=100,000÷Gc (in Pa units).

By way of example and not by limitation, examples of the present disclosure will now be provided.

I. Synthesis of Silyl Diol Ester

General Procedure for bis(chloromethyl)dialkylsilane:

A 500 mL three-necked flask fitted with a reflux condenser and a dropping funnel is charged with 50 mmol of bis(chloromethyl)methylchlorosilane (bis(chloromethyl)dichlorosilane for diethyl derivative) and 200 ml anhydrous ether. 50 mmol (120 mmol for diethyl derivative) of alkylmagnesium chloride/bromide in ether is added to the flask with stirring. The solution is stirred for 30 minutes, and is brought to reflux with heating. Reaction progress is monitored with GC. Upon completion of reaction, the mixture is cooled down to room temperature, and then the flask is placed in an ice-water bath and the reaction is quenched with water. After separation, the aqueous layer is extracted with ether three times. The combined ether extract is washed with brine once, and dried over sodium sulfate. After filtration, the filtrate is concentrated, and the residue is distilled in vacuo to yield a colorless oil. The yields for these preparations are usually about 85%. The $^1$H NMR (500 MHz Brüker) spectral data are shown in Table 3 below.

TABLE 3

Proton NMR Data for Bis(chloromethyl)dialkylsilanes

| Compound | Structure | $^1$H NMR Spectral Data in CDCl$_3$, 500-MHz, δ (ppm) |
|---|---|---|
| Bis(chloromethyl)-dimethylsilane | 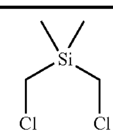 | |
| Bis(chloromethyl)-diethylsilane | 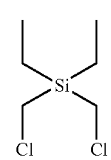 | 2.94 (s, 4H), 1.03 (t, 6H), 0.81 (q, 4H). |
| Bis(chloromethyl)-ethylmethylsilane | 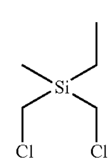 | 2.89 (s, 4H), 0.99 (t, 3H), 0.76 (q, 2H), 0.20 (s, 3H) |
| Bis(chloromethyl)-isobutylmethylsilane | 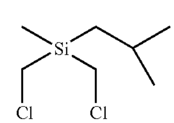 | 2.96 (s, 4H), 1.85 (heptat, 1H), 0.98 (d, 6H), 0.80 (d, 2H), 0.23 (s, 3H) |

Bis(chloromethyl)dimethylsilane was purchased from Gelest, Inc., Morrisville, Pa.

A 500 mL three-necked round bottom flask is charged with 25 mmol of dichlorodimethylsilane, 50 mmol g of bromochloromethane and 150 ml of anhydrous THF. The flask is cooled down to −78° C. with a dry-ice/acetone bath. To this solution is added dropwise 20 ml of a 2.5 M butyl lithium solution in hexanes over a period of 20 minutes. After completion of the addition, the mixture is stirred at this temperature for an additional 20 minutes, and then warmed up to room temperature during 1 h period. The mixture is quenched with a saturated $NH_4Cl$ solution. After separation, the aqueous layer is extracted with ether (3×50 ml), and the combined ether extract washed with brine once and dried with sodium sulfate. After filtration, the filtrate is concentrated. The residue is distilled in vacuo to yield a colorless oil. The yield is about 70%.

General Procedure for Bis(benzoyloxymethyl)dialkylsilane:

A 1000 mL round bottom flask is charged with 0.04 mol of bis(chloromethyl)dialkylsilane, 12.8 g (0.08 mol) of potassium benzoate, and 400 ml of anhydrous DMF. The mixture is heated to 100° C. with vigorous stirring. After 6 to 8 hours, the mixture is cooled to room temperature, and then poured into 400 ml of ice-water. The mixture is extracted with ether (3×200 ml). The combined ether extract is washed with brine once (50 ml) and dried with 50 g of sodium sulfate. After filtration, the filtrate is concentrated and distilled with a Kugelrohr in vacuo or purified by flash column chromatography to yield a colorless oil. The $^1H$ NMR spectral data are shown in Table 4. The yields for these preparations are usually close to 80%.

II. Procatalyst Compositions

A procatalyst precursor is charged, according to the weight shown in Table 5, into a flask equipped with mechanical stirring and with bottom filtration. 60 ml of a mixed solvent of $TiCl_4$ and chlorobenzene (1/1 by volume) is introduced into the flask and then 2.52 mmol of internal electron donor is added. The mixture is heated to the desired reaction temperature (indicated in Table 6) and remains at the same temperature for 60 minutes with stirring at 250 rpm before filtering off the liquid. 60 ml of mixed solvent is added again and the reaction is allowed to continue at the same desired temperature for 60 minutes with stirring followed by filtration. This process is repeated once. 70 ml of iso-octane is used to wash the resultant solid at ambient temperature. After the solvent is removed by filtration, the solid is dried by $N_2$ flow.

TABLE 5

| Procatalyst Precursor | Weight |
| --- | --- |
| MagTi-1 | 3.0 g |
| ME | 3.0 g |
| SHAC ™ 310 | 2.0 g |
| 0074-45-1 | 3.24 g |

MagTi-1 (a MagTi) is a mixed Mg/Ti precursor with composition of $Mg_3Ti(OEt)_8Cl_2$. ME (a MagMo) denotes magnesium ethoxide. SHAC™ 310 is a benzoate-containing procatalyst (a BenMag procatalyst precursor made from a MagTi

TABLE 4

Proton NMR data for silyl diol esters

| Compound | Structure | $^1H$ NMR Spectral Data in $CDCl_3$, δ (PPM) |
| --- | --- | --- |
| Bis(benzoyloxy)dimethylsilane (IED 1) | 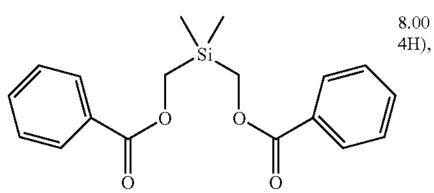 | 8.00 (d, 4H), 7.55 (t, 2H), 7.40 (t, 4H), 4.20 (s, 4H), 0.30 (s, 6H). |
| Bis(benzoyloxy)diethylsilane (IED 2) | 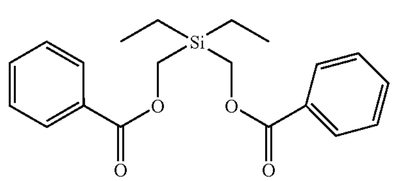 | 8.02 (d, 4H), 7.56 (t, 2H), 7.42 (t, 4H), 4.27 (s, 4H), 1.11 (t, 4H), 0.86 (q, 6H). |
| Bis(benzoyloxy)ethylmethylsilane (IED 3) | 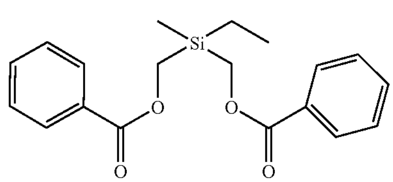 | 8.00 (d, 4H), 7.54 (t, 2H), 7.40 (t, 4H), 4.21 (s, 4H), 1.08 (t, 3H), 0.83 (q, 2H), 0.26 (s, 3H). |
| Bis(benzoyloxy)-isobutylmethylsilane (IED 4) | | 8.00 (d, 4H), 7.54 (t, 2H), 7.40 (t, 4H), 4.20 (s, 4H), 1.92 (heptat, 1H), 1.00 (d, 6H), 0.86 (d, 2H), 0.30 (s, 3H). | procatalyst precursor and an ethyl benzoate internal electron donor) made according to Example 2 in U.S. Pat. No. 6,825,146, the entire content of which is incorporated herein by reference. The compound 0074-45-1 is an EtOH adduct of $MgCl_2$ after partial removal of EtOH at ~90° C. under flowing $N_2$. Ti content for each of the resultant procatalyst compositions is listed in Table 6.

TABLE 6

Procatalyst Compositions

| Description (IED/Precursor) | ID# | Ti % | DiBP wt % | Diol Ester wt % | EB wt % |
|---|---|---|---|---|---|
| IED 1/MagTi@115° C. | 2549-8-1 | 2.33 | | NM | NM |
| IED 1/Mg(OEt)$_2$ @100° C. | 1332-46-3 | 5.24 | | 12.05 | 2.36 |
| IED 1/MgCl$_2$•EtOH @100° C. | 1332-46-4 | 4.04 | | 14.25 | 1.03 |
| *DE/MagTi @115° C. | 1332-45-1 | 2.79 | | NM | 0.11 |
| *DiBP/MagTi @ 115° C. | 2549-8-2 | 2.84 | NM | | |
| *DiBP/MagTi @ 115° C. | 1332-45-2 | 3.22 | 13.56 | | |
| IED 1/SHAC ™ 310 @100° C. | 2521-19-2 | 3.27 | | NM | 0.20 |
| IED 1/SHAC ™ 310 @100° C. | 2549-8-3 | 2.44 | | NM | NM |
| IED 1/SHAC 310 ™ @100° C. | 1332-46-1 | 2.62 | | 15.12 | 0.39 |
| DE/SHAC 310 ™ @100° C. | 1332-45-3 | 2.46 | | NM | 0.45 |
| *DIBP/SHAC 310 ™ @100° C. | 2521-19-3 | 3.49 | 17.62 | | 1.00 |
| *DIBP/SHAC 310 ™ @100° C. | 2549-8-4 | 3.90 | NM | | NM |
| *DIBP/SHAC 310 ™ @100° C. | 1332-44-1 | 3.40 | 23.95 | | 1.20 |
| *DIBP/SHAC 310 ™ @100° C. | 1332-45-4 | 3.80 | 20.59 | | 1.27 |
| IED 2/SHAC 310 ™ @100° C. | 1332-44-2 | 3.19 | | NM | 0.31 |
| IED 3/SHAC 310 ™ @100° C. | 1332-44-3 | 2.86 | | NM | 0.58 |
| IED 4/SHAC 310 ™ @100° C. | 1332-44-4 | 3.06 | | NM | 2.62 |

*= Comparative
DIBP = di-isobutylphthalate
IED = internal electron donor (from Table 4)
DE = 2,2-dimethyl-1,3-propylene glycol dibenzoate
Wt % = based on total weight of procatalyst
NM = Not Measured

III. Polymerization

Polymerization is performed in liquid propylene in a 1-gallon autoclave. After conditioning, the reactors are charged with 1375 g of propylene and a targeted amount of hydrogen and brought to 62° C. External electron donor (either DCPDMS or NPTMS) is added to a 0.27-M triethylaluminum solution in isooctane, a 5.0 wt % catalyst slurry in mineral oil (as indicated in data tables below) and premixed at ambient temperature for 20 minutes before being injected into the reactor to initiate the polymerization. The premixed catalyst components are flushed into the reactor with isooctane using a high pressure catalyst injection pump. After the exotherm, the temperature is controlled to 67° C. Total polymerization time is 1 hour. Catalyst performance and resultant polymer properties are provided in Tables 7-10.

TABLE 7

Performance of Catalysts Made from MagMo and MagTi Procatalyst Precursors

| Procatalyst Description | Catalyst Number | EED | Catalyst (mg) | TEAl (mmol) | Al/ EED | H$_2$ (scc) | Activity (kg/g-hr) | BD (g/cc) | MF | XS (wt %) | PDI | Modulus (kpsi) |
|---|---|---|---|---|---|---|---|---|---|---|---|---|
| IED 1/MagTi@115° C. | 2549-8-1 | DCPDMS | 17.4 | 2.00 | 8 | 2000 | 11.8 | 0.31 | 1.9 | 5.03 | 5.38 | |
| IED 1/Mg(OEt)$_2$ @100° C. | 1332-46-3 | DCPDMS | 14.6 | 2.00 | 8 | 5000 | 8.8 | 0.20 | 79.1 | 7.59 | | |
|  |  |  | 14.6 | 2.00 | 8 | 400 | 6.4 | 0.19 | 2.0 | 8.11 | 6.14 | |
| IED 1/MgCl$_2$•n(EtOH) @100° C. | 1332-46-4 | DCPDMS | 17.4 | 2.00 | 8 | 3000 | 12.9 | 0.32 | 6.8 | 5.88 | | |
|  |  |  | 16.4 | 2.00 | 8 | 400 | 7.6 | 0.31 | 1.4 | 7.96 | 7.73 | |
| *DE/MagTi @115° C. | 1332-45-1 | DCPDMS | 15.7 | 2.00 | 8 | 1870 | 8.9 | 0.23 | 2.0 | 6.02 | 6.85 | |
| *DiBP/MagTi @115° C. | 2549-8-2 | DCPDMS | 11.8 | 2.00 | 8 | 1300 | 39.6 | 0.40 | 4.7 | 3.34 | 4.92 | |
|  | 1332-45-2 | DCPDMS | 11.6 | 2.00 | 8 | 1250 | 38.6 | 0.37 | 5.3 | 3.23 | | 214 |

*= Comparative
DCPDMS = dicyclopentyldimethoxysilane
DIBP = diisobutylphthalate
IED = internal electron donor (from Table 4)
XS = xylene solubles
BD = settled bulk density
DE = 2,2-dimethyl-1,3-propylene glycol dibenzoate
EED = external electron donor
MF = melt flow rate (g/10 minute)

The data in Table 7 shows that procatalysts made using silyl diol ester IED 1 lead to propylene-based polymers having significantly broader PDI when compared to propylene-based polymers produced from a procatalyst containing DiBP as internal electron donor.

TABLE 8

Performance of Catalysts Made from BenMag Procatalyst Precursor

| Procatalyst Description | Catalyst Number | EED | Catalyst (mg) | TEAl (mmol) | Al/ EED | H$_2$ (scc) | Activity (kg/g-hr) | BD (g/cc) | MF | XS (wt %) | PDI | Modulus (kpsi) |
|---|---|---|---|---|---|---|---|---|---|---|---|---|
| IED 1/SHAC ™ | 2521-19-2 | DCPDMS | 16.3 | 1.00 | 4 | 1870 | 22.3 | 0.38 | 0.9 | 2.4 | | |
|  |  |  | 16.3 | 2.00 | 8 | 3740 | 27.9 | 0.41 | 1.1 | 3.52 | | |

TABLE 8-continued

Performance of Catalysts Made from BenMag Procatalyst Precursor

| Procatalyst Description | Catalyst Number | EED | Catalyst (mg) | TEAl (mmol) | Al/ EED | H₂ (scc) | Activity (kg/g-hr) | BD (g/cc) | MF | XS (wt %) | PDI | Modulus (kpsi) |
|---|---|---|---|---|---|---|---|---|---|---|---|---|
| 310 @ 100° C. | | | 16.3 | 2.00 | 8 | 7480 | 24.1 | 0.39 | 9.4 | 3.18 | | |
| | | | 16.3 | 1.00 | 4 | 7480 | 24.4 | 0.37 | 7.0 | 3.80 | | |
| | | | 16.3 | 1.00 | 4 | 3740 | 24.0 | 0.39 | 0.5 | 2.78 | | |
| | | NPTMS | 16.3 | 1.00 | 4 | 1400 | 22.1 | 0.39 | <0.2 | 1.88 | | |
| | | | 16.3 | 2.00 | 8 | 2800 | 23.5 | 0.41 | 0.4 | 2.63 | | |
| | | | 16.3 | 2.00 | 8 | 5600 | 21.0 | 0.40 | 5.3 | 2.75 | | |
| | | | 16.3 | 2.00 | 8 | 2800 | 22.5 | 0.40 | 1.4 | 2.94 | | |
| | | | 16.3 | 1.00 | 4 | 5600 | 20.4 | 0.39 | 2.9 | 2.49 | | |
| | 2549-8-3 | DCPMS | 11.8 | 2.00 | 8 | 5000 | 28.4 | 0.40 | 4.1 | 3.11 | | |
| | | | 11.8 | 2.00 | 8 | 7400 | 29.0 | 0.41 | 5.6 | 3.18 | 7.03 | |
| | 1332-46-1 | DCPDMS | 16.1 | 2.00 | 8 | 5000 | 31.8 | 0.39 | 3.3 | 3.21 | | 248 |
| DE/SHAC ™ | 1332-45-3 | DCPDMS | 10.6 | 2.00 | 8 | 15500 | 28.3 | 0.40 | 43.8 | 4.09 | | |
| 310 @100° C. | | | 10.6 | 2.00 | 8 | 5000 | 26.5 | 0.41 | 1.7 | 3.64 | 7.16 | 253 |
| | | | 12.8 | 2.00 | 8 | 10000 | 24.6 | 0.39 | 11.8 | 2.47 | | |
| | 2521-19-3 | NPTMS | 16.4 | 1.00 | 4 | 1400 | 19.7 | 0.39 | 4.9 | 3.69 | | |
| | | DCPDMS | 16.4 | 1.00 | 4 | 1870 | 24.9 | 0.38 | 3.0 | 3.29 | | |
| DIBP/SHAC ™ | 2549-8-4 | DCPDMS | 17.4 | 2.00 | 8 | 2000 | 28.9 | 0.40 | 2.6 | 3.78 | 5.26 | |
| 310 @100° C. | | | 9.3 | 2.00 | 8 | 1300 | 33.0 | 0.41 | 3.3 | 3.19 | 4.61 | |
| | 1332-44-1 | DCPDMS | 11.3 | 2.00 | 8 | 1200 | 30.0 | 0.38 | 2.0 | 3.73 | | 216 |
| | 1332-45-4 | DCPDMS | 11.3 | 2.00 | 8 | 1870 | 34.4 | 0.39 | 11.1 | 4.25 | | |
| | | | 11.3 | 2.00 | 8 | 850 | 28.0 | 0.40 | 2.5 | 3.59 | 4.96 | 231 |
| | | | 11.3 | 2.00 | 8 | 900 | 26.3 | 0.40 | 2.3 | 3.28 | 5.06 | 232 |

BD = settled bulk density
DE = 2,2-dimethyl-1,3-propylene glycol dibenzoate
EED = external electron donor
MF = melt flow rate (g/10 minute)
XS = xylene solubles
DCPDMS = dicyclopentyldimethoxysilane
DIBP = di-isobutylphthalate
IED = internal electron donor (from Table 4)
NPTMS = n-propyltrimethoxysilane Comparison of data in Table 7 and Table 8 indicate that catalyst activity and steroselectivity are improved by using a benzoate-containing magnesium chloride (BenMag) precursor while the broad PDI is maintained for both of silyl diol ester (IED 1) or simple diol ester (DE) internal donors. In addition, there is a significant improvement in both PDI and flexural modulus for both of IED 1 and DE internal donors compared to DiBP-based catalyst.

TABLE 9

Performance of Catalysts with BenCat Precursor and Silyl Diol Ester Internal Donor

| Procatalyst Description | Catalyst Number | EED | Catalyst (mg) | TEAl (mmol) | Al/ SCA | H₂ (scc) | Activity (kg/g-hr) | BD (g/cc) | MF | XS (wt %) | PDI | Modulus (kpsi) |
|---|---|---|---|---|---|---|---|---|---|---|---|---|
| IED 1/SHAC 310 | 2521-19-2 | DCPDMS | 16.3 | 1.00 | 4 | 1870 | 22.3 | 0.38 | 0.93 | 2.4 | | |
| @ 100° C. | | | 16.3 | 2.00 | 8 | 3740 | 27.9 | 0.41 | 1.13 | 3.52 | | |
| | | | 16.3 | 2.00 | 8 | 7480 | 24.1 | 0.39 | 9.39 | 3.18 | | |
| | | | 16.3 | 1.00 | 4 | 7480 | 24.4 | 0.37 | 6.96 | 3.80 | | |
| | | | 16.3 | 1.00 | 4 | 3740 | 24.0 | 0.39 | 0.51 | 2.78 | | |
| | | NPTMS | 16.3 | 1.00 | 4 | 1400 | 22.1 | 0.39 | <0.22 | 1.88 | | |
| | | | 16.3 | 2.00 | 8 | 2800 | 23.5 | 0.41 | 0.41 | 2.63 | | |
| | | | 16.3 | 2.00 | 8 | 5600 | 21.0 | 0.40 | 5.34 | 2.75 | | |
| | | | 16.3 | 1.00 | 4 | 2800 | 22.5 | 0.40 | 1.40 | 2.94 | | |
| | | | 16.3 | 1.00 | 4 | 5600 | 20.4 | 0.39 | 2.89 | 2.49 | | |
| | 2549-8-3 | DCPMS | 11.8 | 2.00 | 8 | 5000 | 28.4 | 0.40 | 4.12 | 3.11 | | |
| | | | 11.8 | 2.00 | 8 | 7400 | 29.0 | 0.41 | 5.60 | 3.18 | 7.03 | |
| | 1332-46-1 | DCPDMS | 16.1 | 2.00 | 8 | 5000 | 31.8 | 0.39 | 3.27 | 3.21 | | 248 |
| IED 2/SHAC 310 | 1332-44-2 | DCPDMS | 15.3 | 2.00 | 8 | 1870 | 31.8 | 0.41 | 0.39 | 2.73 | | |
| @100° C. | | | 15.3 | 2.00 | 8 | 5000 | 20.9 | 0.41 | 2.34 | 1.40 | 6.88 | 269 |
| | | | 10.2 | 2.00 | 8 | 10000 | 34.2 | 0.40 | 10.79 | 3.28 | 6.93 | 270 |
| IED 3/SHAC 310 | 1332-44-3 | DCPDMS | 15.0 | 2.00 | 8 | 1870 | 40.2 | 0.41 | 0.40 | 1.82 | | |
| | | | 14.8 | 2.0 | 4 | 1870 | 45.8 | 0.39 | 0.13 | 2.13 | | |
| | | | 9.9 | 2.00 | 4 | 2750 | 42.3 | 0.41 | 1.57 | 3.00 | 6.56 | 250 |
| IED 4/SHAC 310 | 1332-44-4 | DCPDMS | 9.9 | 2.00 | 8 | 3000 | 38.5 | 0.40 | 1.20 | 2.97 | 6.29 | 246 |
| @100° C. | | | 9.9 | 2.00 | 8 | 4500 | 34.4 | 0.42 | 3.77 | 3.13 | 6.57 | 252 |
| | | | 9.9 | 2.00 | 8 | 5000 | 42.4 | 0.42 | 4.17 | 3.82 | 6.25 | 262 |
| | | | 9.9 | 2.00 | 8 | 5000 | 32.3 | 0.38 | 4.73 | 2.78 | 6.33 | |

TABLE 9-continued

Performance of Catalysts with BenCat Precursor and Silyl Diol Ester Internal Donor

| Procatalyst Description | Catalyst Number | EED | Catalyst (mg) | TEAl (mmol) | Al/SCA | H$_2$ (scc) | Activity (kg/g-hr) | BD (g/cc) | MF | XS (wt %) | PDI | Modulus (kpsi) |
|---|---|---|---|---|---|---|---|---|---|---|---|---|
| | | | 9.9 | 2.00 | 8 | 1000 | 40.5 | 0.41 | 18.31 | 2.81 | | |
| | | | 7.9 | 2.00 | 8 | 15000 | 34.9 | 0.40 | 53.34 | 3.58 | | |
| | | | 7.9 | | | 17500 | 27.1 | 0.37 | 173.32 | 4.78 | | |

BD = settled bulk density
EED = external electron donor
MF = melt flow rate (g/10 minute)
XS = xylene solubles
DCPDMS = dicyclopentyldimethoxysilane
IED = internal electron donor (from Table 4)
NPTMS = n-propyltrimethoxysilane Data in Table 9 shows that catalyst activity and steroselectivity can be modified by changing the structure of silyl diol ester, while the catalyst performance and polymer properties remain differentiated from the DiBP-based catalyst.

It is specifically intended that the present disclosure not be limited to the embodiments and illustrations contained herein, but include modified forms of those embodiments including portions of the embodiments and combinations of elements of different embodiments as come within the scope of the following claims.

We claim:

1. A procatalyst composition comprising:
a combination of a magnesium moiety, a titanium moiety, and an internal electron donor, the internal electron donor comprising a silyl ester of the structure

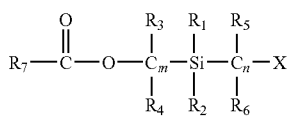

wherein m is 1 denoting a hydrocarbyl with the same number of carbon atoms, n is 1 denoting a hydrocarbyl with same number of carbon atoms, R$_1$-R$_7$ are the same or different and each is selected from the group consisting of hydrogen, a substituted hydrocarbyl group having 1 to 20 carbon atoms, an unsubstituted hydrocarbyl group having 1 to 20 carbon atoms, and combinations thereof; and X is an electron donating group.

2. The procatalyst composition of claim 1 wherein X is selected from the group consisting of —C(=O)OR, —O(O=)CR, —(O=)CNHR, —(O=)CNRR', —NH(O=)CR, —NR'(O=)CR, —C(=O)R, —OR, —NHR, —NR'R, —SR, —OP(OR')(OR), —OP(=O)(OR')(OR), —S(=O)R, —S(=O)$_2$R, —OS(=O)$_2$(OR), and combinations thereof; and R and R' are the same or different and each of R and R' is selected from the group consisting of a substituted hydrocarbyl group having 1 to 20 carbon atoms, an unsubstituted hydrocarbyl group having 1 to 20 carbon atoms, and combinations thereof.

3. The procatalyst composition of claim 1 comprising an internal electron donor of the structure

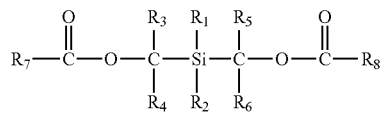

wherein R$_1$-R$_8$ are the same or different and each is selected from the group consisting of hydrogen, a substituted hydrocarbyl group having 1 to 20 carbon atoms, an unsubstituted hydrocarbyl group having 1 to 20 carbon atoms, and combinations thereof.

4. The procatalyst composition of claim 1 comprising an internal electron donor of the structure

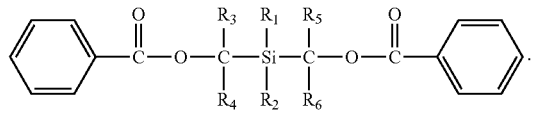

5. The procatalyst composition of claim 1 wherein R$_3$-R$_6$ are hydrogen, R$_1$ and R$_2$ are the same or different and each is selected from the group consisting of hydrogen, a C$_1$-C$_6$ alkyl group, and combinations thereof.

6. The procatalyst composition claim 1 wherein each of R$_1$ and R$_2$ is selected from the group consisting of methyl, ethyl, n-propyl, i-propyl, n-butyl, i-butyl, t-butyl, and combinations thereof.

7. The procatalyst composition of claim 1 wherein R$_1$ and R$_2$ are both methyl.

8. The procatalyst composition of claim 1 wherein R$_1$ is methyl and R$_2$ is ethyl.

9. The procatalyst composition of claim 1 wherein R$_1$ and R$_2$ are both ethyl.

10. The procatalyst composition of claim 1 wherein R$_1$ is methyl and R$_2$ is isobutyl.

11. The procatalyst composition of claim 1 wherein the silyl ester comprises bis(benzoyloxy)dimethylsilane.

12. The procatalyst composition of claim 1 wherein the silyl ester comprises bis(benzoyloxy)diethylsilane.

13. The procatalyst composition of claim 1 wherein the silyl ester comprises bis(benzoyloxy)ethylmethylsilane.

14. The procatalyst composition of claim 1 wherein the silyl ester comprises bis(benzoyloxy)isobutylmethylsilane.

15. A catalyst composition comprising:

a procatalyst composition of claim 1; and a cocatalyst.

16. The catalyst composition of claim 15 comprising a member selected from the group consisting of an external electron donor, an activity limiting agent, and combinations thereof.

* * * * *